(12) United States Patent
Vail, III et al.

(10) Patent No.: US 6,896,653 B1
(45) Date of Patent: May 24, 2005

(54) PERSONAL PELVIC VIEWER

(75) Inventors: William Banning Vail, III, Bothell, WA (US); Marilyn L. Vail, Bothell, WA (US)

(73) Assignee: Science for Medical Advocates, Inc., Woodinville, WA (US)

( * ) Notice: Subject to any disclaimer, the term of this patent is extended or adjusted under 35 U.S.C. 154(b) by 0 days.

(21) Appl. No.: 10/384,448

(22) Filed: Mar. 7, 2003

Related U.S. Application Data

(60) Provisional application No. 60/362,567, filed on Mar. 7, 2002.

(51) Int. Cl.[7] .............................................. A61B 1/307
(52) U.S. Cl. ......................... 600/135; 600/109; 600/118
(58) Field of Search ................................ 600/117, 135, 600/103, 109, 110, 112, 118, 220, 160, 167, 168, 176, 183

(56) References Cited

U.S. PATENT DOCUMENTS

2001/0035902 A1 * 11/2001 Iddan et al. .................. 348/76
2003/0083590 A1 * 5/2003 Hochman et al. ............ 600/549
2003/0181788 A1 * 9/2003 Yokoi et al. ................. 600/160
2003/0228553 A1 * 12/2003 Mandelkern et al. ......... 433/29

* cited by examiner

Primary Examiner—Beverly M. Flanagan

(57) ABSTRACT

The Personal Pelvic Viewer™ abbreviated PPV™ is a hand-held instrument which a woman may place by herself into her own vagina to conveniently view and record video images of the interior of her vagina and cervix on a remote monitor, such as a television, computer display, or computer monitor. The PPV possesses a sealed video camera and may obtain its battery power through a short cable to a remote transceiver unit which also provides a wireless communication link to a base station transceiver which in turn provides the video information to be displayed on the television, computer display, etc. The PPV provides a convenient instrument that allows a lone female to observe the interior of her own vagina in total privacy for medical reasons, to determine her own fertility, and to observe her sexual response.

29 Claims, 3 Drawing Sheets

PERSONAL PELVIC VIEWER

CROSS-REFERENCES TO RELATED APPLICATIONS

This application relates to Provisional Patent Application No. 60/362,567, having the Filing Date of Mar. 7, 2002, that is entitled "Personal Pelvic Viewer", an entire copy of which is incorporated herein by reference. Applicant claims priority from this Provisional Patent Application No. 60/362,567.

Provisional Patent Application No. 60/362,567 is related to U.S. Disclosure Document No. 470975, having the filing date of Mar. 15, 2000, that is entitled "Personal Pelvic Viewer", an entire copy of which is incorporated herein by reference. An entire copy of this U.S. Disclosure Document 470975 has been retained by the Disclosure Document Program that now has Retention Label 60/362,567 with the "Filing Date" of Mar. 3, 2002 in Technology Center 0500 in accordance with the Mar. 20, 2002 letter from Ms. Genet Teferra of the Disclosure Document Program.

BACKGROUND OF THE INVENTION

1. Field of the Invention

The field of invention relates to methods and apparatus that allow a lone human female to conveniently obtain and record video images from within her own vagina and video images of her own cervix. Such private video images are useful to enhance the privacy of the female during self-examinations, to help her gain additional power over her own body, to help her determine potential early warning signs of cervical cancer or infections, for birth control, to aid in becoming pregnant, and for educational proposes to view and study her own sexual response. The hand-held device, or instrument, that is inserted within the vagina is called the Personal Pelvic Viewer™ (PPV™) which contains a sealed video camera.

2. Description of the Prior Art

Various vaginal specula are used by physicians to view the interior of the vagina of a patient as summarized in FIGS. 8A, 8B, 8C, and 8D and 9 of U.S. Pat. No. 5,865,729 that issued on Feb. 2, 1999. A transparent bag placed over a video camera has been used by physicians for medical uses as shown in U.S. Pat. No. 5,971,916 that issued on Oct. 26, 1999. Vaginal specula for use by physicians are illuminated with a fiber-optic illuminating system as shown in U.S. Pat. No. 4,597,383 that issued on Jul. 1, 1986. Different probes used by physicians with vaginal specula are shown in European Patent Application 0 650 694 A1 that was published on May 3, 1995. A vaginal speculum used by a physician is refitted with a video camera as shown in U.S. Pat. No. 5,026,368 that issued on Jun. 25, 1991. A vaginal speculum used by a physician is also retrofitted with a video camera as shown in European Patent No. 0 451 200 B1 that issued on Nov. 8, 1995. Another vaginal speculum used by a physician is retrofitted with a video camera as shown in U.S. Ser. No. 2001/0,056,223 A1 that was published on Dec. 27, 2001. A video cervicoscope system to be used by physicians is shown in European Patent Application No. 0 426 063 A1 published on May 8, 1991. A cervical videoscope with a detachable camera unit used by physicians is shown in European Patent EP 0 585 321 B1 that issued on Jan. 29, 1997. An apparatus used by physicians for digital photography useful in cancer detection is shown in U.S. Pat. No. 5,989,184 that issued on Nov. 23, 1999. However, the prior art does not provide methods or apparatus so that a female alone may conveniently view the interior of her own vagina and view her own cervix.

SUMMARY OF THE INVENTION

An object of the invention is to provide a lone female at home apparatus to conveniently view the interior of her own vagina and her own cervix.

Another object of the invention is to provide a lone female at home a method to conveniently view the interior of her own vagina and her own cervix.

Yet another object of the invention is to provide females the power to inspect their own interior reproductive organs that include the vagina and the cervix without the necessity of the presence of another individual.

Another object of the invention is to provide individual females additional power over their own bodies by being able to conveniently view the interior of selected portions of their own reproductive organs including the vagina and the cervix.

Yet another object of the invention is to provide an individual female at home apparatus to obtain video recordings of the interior of her own vagina and her own cervix.

A further object of the invention is to provide an individual female at home methods to obtain video recordings of the interior of her own vagina and her own cervix.

Another object of the invention is to provide an individual female at home apparatus to obtain single, or multiple, photographs of the interior of her own vagina and her own cervix.

Yet another object of the invention is to provide an individual female at home methods to obtain single, or multiple, photographs of the interior of her own vagina and her own cervix.

A further object of the invention is to provide methods and apparatus for a lone female at home to inspect her own vagina and cervix to determine any infections that may be visually present.

Another object of the invention is to provide methods and apparatus for a lone female at home to inspect her own vagina and cervix to determine any infections that may be visually present and as a result of early detection, the ability to request immediate assistance from a health professional that could lead to better outcomes at lower cost due to early detection of potential infections.

Yet another object of the invention is to provide methods and apparatus for a lone female at home to inspect her own vagina and cervix to determine any infections that may be caused by an IUD.

Still another object of the invention is to provide methods and apparatus for a lone female at home to inspect her own vagina and cervix to determine any infections that may be caused by bacterial, viruses, or fungi.

A further object of the invention is to provide methods and apparatus for a lone female at home to inspect her own cervix for the possible early warning signs of cervical cancer.

Another object of the invention is to provide methods and apparatus for a lone female at home to inspect her own cervix to determine any visual early warning signs of cervical cancer that may be visually present and as a result of early detection, the ability to request immediate assistance from a health professional that could lead to better outcomes at lower cost due to early detection of possible cervical cancer.

Yet another object of the invention is to provide methods and apparatus for a lone female at home to inspect and record the visual appearance of her cervix during her monthly cycle so as to determine any departures from the normal appearance from month to month that may be an indication of the onset of cervical cancer or other health care problems.

A further object of the invention is to provide methods and apparatus for a lone female at home to inspect her own vagina and cervix to determine the presence of any foreign objects, including misplaced tampons, or condoms that may have slipped off during intercourse.

Another object of the invention is to provide methods and apparatus for a lone female at home to inspect her own vagina and cervix for educational purposes.

Yet another object of the invention is to provide methods and apparatus for a lone female at home to obtain video recordings of her own vagina and cervix that may be forwarded by the internet to her physician for additional professional review.

A further object of the invention is to provide methods and apparatus for a lone female at home to view images of the interior of her vagina, her cervix, and color and texture of her cervical mucus to optimize chances of becoming pregnant.

Another object of the invention is to provide methods and apparatus for a lone female at home to view images of the interior of her vagina, her cervix, and the color and texture of her cervical mucus to optimize chances of preventing pregnancy.

Yet another object of the invention is to allow a female to obtain images from within her own vagina and her cervix and display those images on a television set.

A further object of the invention is to allow a female to obtain images from within her own vagina and her cervix and display those images on a computer display terminal.

Another object of the invention is to obtain visual images from an self-contained video camera located within the vagina and to forward those images via wireless communication technology to a display unit, where the wireless communication link includes any type of infra-red, radio wave, or microwave wireless communication link.

Yet another object of the invention is to allow a lone female to obtain visual images from within her vagina and of her cervix during her sexual cycle while privately masturbating for educational proposes so as to better understand her own excitement phase, plateau phase, orgasm phase, and resolution phase.

A further object of the invention is to allow a lone female to record video images from within her vagina and of her cervix during her sexual cycle while privately masturbating for educational proposes to better understand her own excitement phase, plateau phase, orgasm phase, and resolution phase.

Another object of the invention is to allow to a lone female to conveniently record video images from within her vagina and view of her cervix while privately masturbating that may be provided at a later time to other health professionals to diagnose certain types of infertility problems.

Yet another object of the invention is to provide methods and apparatus where in additional to the recordings of images within the vagina and cervix, readings of temperature vs. time, pressure vs. time, sound vs. time, and ph vs. time, may also be obtained for a variety of different educational and medical reasons.

A finally, another object of the invention is to provide a convenient apparatus for a lone female to privately perform self-examination of her own vagina and her own cervix, which apparatus is called the Personal Pelvic Viewer™ (PPV™).

DESCRIPTION OF THE PREFERRED EMBODIMENTS

Figure 1:
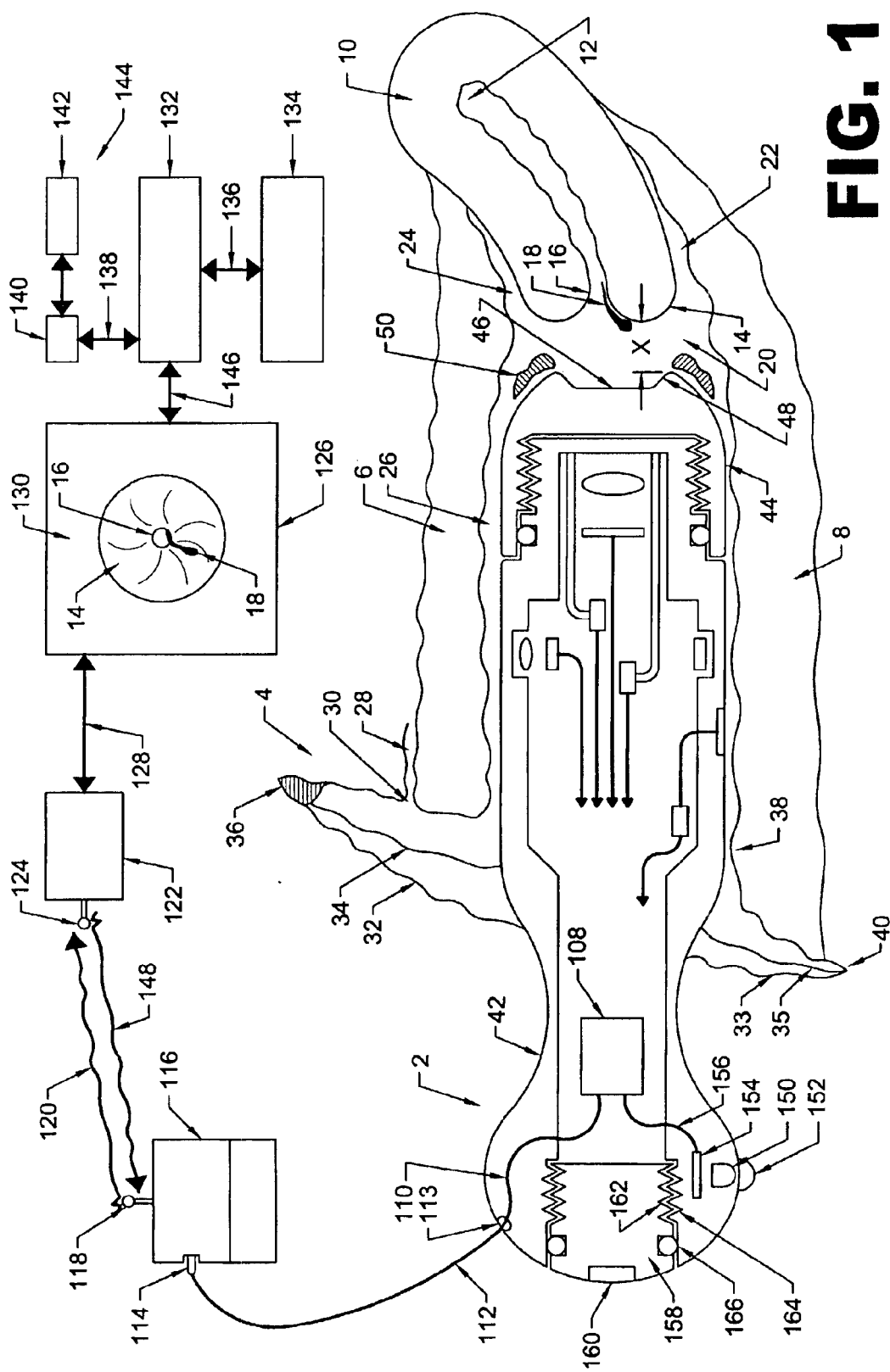
FIG. 1 shows a section view of a preferred embodiment of the Personal Pelvic Viewer (PPV) that provides video images from the interior of the vagina and of the cervix.

Many of the reproductive organs of the human male are easily viewed and inspected by the male because of their location on the exterior of the male torso. However, most of the reproductive organs of the human female are not easily viewed and inspected by the female herself because of their predominant location on the interior of the female torso. As a consequence, many females must routinely undergo typical pelvic examinations. For a description of such pelvic examinations, see Luckmann, 1997, in the section entitled "Procedure 31-1, Pelvic Examination", pages 1449–1454". Please also refer to Scott, et. al, 1999, pages 523–526.

A clear photographic record of the pelvic examination performed by a medical professional with a bivalve speculum appears in Edge and Miller, 1994, page 24. This type of record is relatively hard to find in the literature on the subject.

Typical recommendations include a minimum of one pelvic examination per year for the female during her reproductive years, and perhaps fewer examinations following a "hysterectomy for benign disease" (Scott, et. al, 1999, page 526). During a pelvic examination, a health professional, most often a male gynecologist, views the interior genitalia of the female patient while the female patient is in the so-called lithotomy position with her feet in the stirrups of an examination table. This procedure has been described as typically making women "nervous" because of various "horror stories" which is an "embarrassing" procedure to some women (Lauersen, et. al, 1987, page 43). Then, the gynecologist describes to the female his findings and opinions concerning the examination of her own body.

It is well known that the appearance of the cervix is dramatically affected by the woman's reproductive cycle. See for example, Gage, 1995, and the many photographs following page 128. These photographs show that the color, shape, texture, etc. of the cervix and other internal organs change during the monthly cycle. Dramatic changes also occur during early pregnancy, under the influence of infections and disease, and in response to a wide variety of other circumstances.

It is the opinions of the inventors that, in general, the gynecologist is under a severe handicap in determining any visual changes to the cervix and vagina of a given woman patient as an advanced warning to diseases, such as cancer, and other maladies. If the woman only sees the gynecologist about once a year, then how would the gynecologist remember what the particular female looked like? How would he, or she, remember from the thousands of pelvic examinations any detailed coloration that might foretell problems? Further, if the female comes in the office during different portions of her menstrual period, and because of the variability of the appearance her reproductive organs during her period, then any chance of observing visual changes as an indicator of problems is further reduced. It is the opinions of the inventors that most gynecologists have little way of reliability knowing what is "normal" for a given female patient—much to the detriment of the health of the female patient.

The inventors believe that once a female has in her possession the means to determine what she looks like inside own her vagina, and if she knows the appearance of her cervix repeatedly during the same portions of her period, then it may be possible for the given patient herself to determine from her own visual records that changes have occurred that may foretell major illness.

It might be worthwhile to consider the following analogy. W. Banning Vail, Ph.D. noticed from the odd appearance of the skin on his neck that he had skin cancer. This odd appearance included visual changes in the coloration, texture, and observable structure of the skin. It was obvious something was wrong with the skin. The type of cancer was basal cell carcinoma, and it was surgically removed. W. Banning Vail, Ph.D. visually inspects his own penis on occasion for signs of cancer of the type described in Luckmann, 1997, page 1436. It is also suggested that all males perform "Testicular Self-Examinations TSE". Again, see Luckmann, 1997, page 1436. Then, why should the human female not have the means to make similar observations herself? The male is recommended to view his own genitalia for health reasons. By analogy, therefore, it is likely that if such technology already existed, then it is the opinions of the inventors that females would receive similar suggestions. However, that technology does not exist for the female herself to conveniently view the interior of her vagina and her cervix.

The inventors therefore suggest that when women are given the power to conveniently inspect their own internal reproductive organs that it is possible that many of them could detect changes in their interior reproductive organs that may forewarn them against possible disease, infections, etc. in analogous fashions to what males are now able to do for themselves.

It has heretofore been possible with extraordinary effort for a woman to perform a pelvic self-examination using a standard bivalve speculum, a mirror, and light. However, this requires considerably dexterity. For example, please see the text and photographs in Sloane, 1993, in the section entitled "Vaginal Self-Examination", pages 281–285. The following quote is from page 284 of that reference:

"Why Self-Examination? Why Not? There are many reasons for self-examination—there are health and financial benefits for women. Women who are acquainted with the normal appearance of their external genitalia and vaginal and cervical anatomy may be able to detect changes that indicate a developing pathology in its early stages. An infection caught early is easier, safer, and cheaper to treat than a full-blown case of itching vaginitis, for example."

That same reference goes on to state with regards to self-examination and mutual-examination ". . . is another way of demystifying the practice of medicine and gaining more control over their bodies." With regards to self-examination and mutual-examination: "It is a tool that can be used to take the dominance and mystery out of the doctor's role." Further, it states: "When the doctor stands less huge and all knowing, and the women lies less confused and troubled, the difference in power between them is reduced. Women must find the confidence, however possible, for a more equalized relationship between themselves and their physicians . . . ".

For such vaginal self-examination, please also refer to the photographs and text in the book entitled "Our Bodies, Ourselves for the New Century", 1998, page 593. The following quote is from that page:

'For some women, placing the speculum and finding the cervix may take some effort. Breathe deeply and manipulate the speculum gently while looking into the mirror. Focus the light source on the mirror to help you see better. (A friend can help with this.) With the speculum in the correct position, you will be able to see both the folds in the vaginal walls and your cervix, which looks pink, bulbish, and wet. (If your are pregnant, your cervix will have a bluish tint; if your are menopausal or nursing, it may be quite pale.) Depending on where you are in your menstrual cycle, your secretions may be white and creamy or clear and stretchy. By learning what is "normal" for you, you will more easily be able to identify any changes that may indicate ovulation, an infection, or pregnancy.'

This particular reference goes step-by-step into the contortions that a female must do to view her own cervix. That reference suggests getting a friend to help. To say the least, it is certainly difficult for the woman to routinely view her internal reproductive organs using a bivalve speculum, mirror, and light.

A purpose of this invention is to describe the "Personal Pelvic Viewer™" or "PPV™". One purpose of this device is to allow a woman to closely examine and monitor her own cervix in the privacy of her own home when she wishes to do so. Various embodiments of the invention allow her to record her observations on a computer or on a VCR attached to a TV monitor. Entirely at the option of the female, her observations may be taken by her in various forms for presentation to her doctor to document any problems which might develop. The inventors are not precluding in any way the use of this device by the professional medical community for a variety of purposes.

Perhaps much can be learned from the situation involving breast self-examination (BSE). For example, Rosenfeld, 1997, on page 689 states: "Breast self-examination is advocated as a low-cost method for breast cancer detection. However, BSE has not been specifically evaluated in randomized clinical trials. Some observational studies suggest that women who perform BSE have lower breast cancer mortality rate than those who do not (75)." Further, Planned Parenthood Federation of America, Inc., 1996, states on page 69: "The breast self-examination (BSE) is a self-help tool that makes finding suspicious lumps more likely. Some 80% of breast cancers are first detected by the woman through BSE". Accordingly, despite the vast resources, instrumentation, and attention provided by physicians during physical examinations to the detection of breast cancer, it is the women themselves that locate troubles in about 80% of the cases.

In the case of BSE, Planned Parenthood Federation of America, Inc., 1996, further states on page 69:

"Perform BSE every month so you can get to know your breasts and what regular changes they go through in conjunction with your menstrual cycle. Many women prefer doing the BSE in the shower or bathtub, since fingers slide readily over wet and soapy skin, making it easier to detect changes.

Since early detection improves the success of cancer treatment, especially if the cancer is caught in the early stages, it is important to seek medical attention immediately if a lump is found. Do not wait until the end of the next menstrual cycle to see if a lump or thickening is due only to menstrual-related changes."

By analogy, the inventors believe that if a woman can conveniently inspect the interior of her own vagina and cervix once a month, that many women will be able to spot trouble signs early. Once spotting trouble, or any changes, the women could then immediately seek the advice of the medical community. If women had access to the PPV, the inventors would not be surprised if they were able to spot trouble early in analogy with the situation involving breast cancer, where women detect 80% of the cases themselves despite the vast resources devoted by the medical community to examinations, machines, and tests.

The inventors also wish to point out that Luckmann, 1997 advocates teaching women to perform vulval self-examination. Page 1455 from Luckmann, 1997 states the following:

"Learning/Teaching Guidelines for Vulvar Self-Examination Overview

1. Explain why monthly examination of the vulvar area is important.
2. Teach the woman to perform the examination between menstrual periods.
3. Remind the woman that most signs and symptoms do not mean cancer but that early detection of vulvar cancer usually means cure if it is treated early.

Technique of Examination

1. Assist the woman to find a comfortable position—on the edge of her bed or bathtub or on the floor—in a well-lighted area (or use a flashlight).
2. Instruct her to use a hand mirror to examine the external genitalia.
3. Point out the genital organs that make up the vulvar area.
4. Assist the woman in examining the area around the vaginal opening from the mons pubis to the anus.
5. Instruct the woman to palpate as well as look at the vulvar area.
6. Instruct the woman to report any lumps, masses, growths, sores, changes in skin color, painful areas, or itching to her health care provider."

Accordingly, if self-examination of the breasts is suggested by the medical community, and if self-examination of the external genitalia are suggested by the medical community, then why not self-examination of the internal genitalia? Of course, the reason that this is not a routine option is because of the current difficulty in performing pelvic self-examinations. The use of the PPV will allow such pelvic self-examinations to become routine, should a female choose to do so.

So, what evidence do the inventors have that women might be able to detect problems if they had a PPV? As just one example, see the photograph on the lower right-hand side on the page immediately proceeding page 129 of Gage, 1995. There it states:

"In this photo, an IUD string can be seen coming out of the os. The whitish part of the string at the os is where bacteria have gathered, like a pus in an infection. This woman's IUD is a Dalkon Shield, a type that has been removed from the market in the U.S. because of the number of deaths and severe infections associated with it. (It is now recommended that every woman who has a Dalkon Shield have it removed.) She is 31 years old. The red spots above her os are irritations commonly seen on the cervixes of women who have IUD's."

Just look at the photograph. It is the opinions of the inventors that had the female been able to inspect here own uterus, that she could have spotted infection turning a healthy appearing cervix into what is observed.

Marilyn L. Vail had a similar problem with an IUD approximately 30 years ago. To the best of her knowledge, she received the now infamous Dalkon Shield. Her primary gynecologist refused to remove the IUD when it began causing her pain and discomfort immediately after it was placed in her uterus. The male gynecologist simply stated that she "needed to get used to it". Marilyn L. Vail then had to go to another gynecologist, a female gynecologist, who removed it. By that time, the IUD had caused a severe infection and had partially imbedded into the wall of Marilyn's uterus. Then a sequence of events transpired rapidly spanning about one year that included Marilyn L. Vail developing a new, and very painful, condition of endometrioses that was then "cured" by the surgical removal of her uterus and other organs by the same male gynecologist that refused to remove the IUD—that apparently was at least a major contributing cause of the problem, or the entire cause of the problem, for all we now know. Suppose, however, that Marilyn L. Vail could have routinely viewed her own cervix at that time. Suppose further that she could have monitored her own cervix before, and after, the insertion of the IUD. Under these circumstances, could she have immediately observed the commencement of the disastrous infection associated with the IUD? We believe so. It is our opinions that had Marilyn L. Vail been able to observe her own cervix, then perhaps much pain, agony, and a now questionable hysterectomy could have been entirely avoided. The apparent arrogance of her initial male attending physician, her lack of knowledge of her own body, and the lack of any definitive scientific observations available to her led to a long time delay that eventually required the surgical removal of many of her reproductive organs. In our opinions, this is a typical situation that has been repeatedly inflicted on many women. In our opinions, this ongoing situation is simply unacceptable, and something needs to be done now.

The inventors are therefore dedicated to inventing devices that allow an individual female alone in the privacy of her own home to conveniently view, and record if she chooses, her own cervix and the interior of her own vagina. This is certainly useful for educational purposes—if for no other reason. If the female chooses to record what she views, perhaps under certain circumstances she might wish to share this data with her doctor or gynecologist to assist the medical professionals to diagnose any problems that might develop. If the female patient were to arrive in her doctors office with clear, absolute, and undeniable evidence of physical changes that accompanied the onset of symptoms then perhaps fewer male doctors, in particular, would suggest that whatever ailed the female was simply "in her head". With scientific evidence in her own hands, it would be more difficult for the attending male physician, for the most part, to send the female home accompanied by some condescending comments. With evidence and knowledge in her own hands, the female would have the power to demand immediate attention to her medical problems.

There are many other uses for the Personal Pelvic Viewer including providing information that may be useful to optimize the chances of becoming pregnant. Alternatively, the Personal Pelvic Viewer may be used by the female to better understand and monitor her body when attempting to follow the so-called "rhythm method" for family planning purposes.

Detailed Description of the Personal Pelvic Viewer (PPV)

Figure 2:
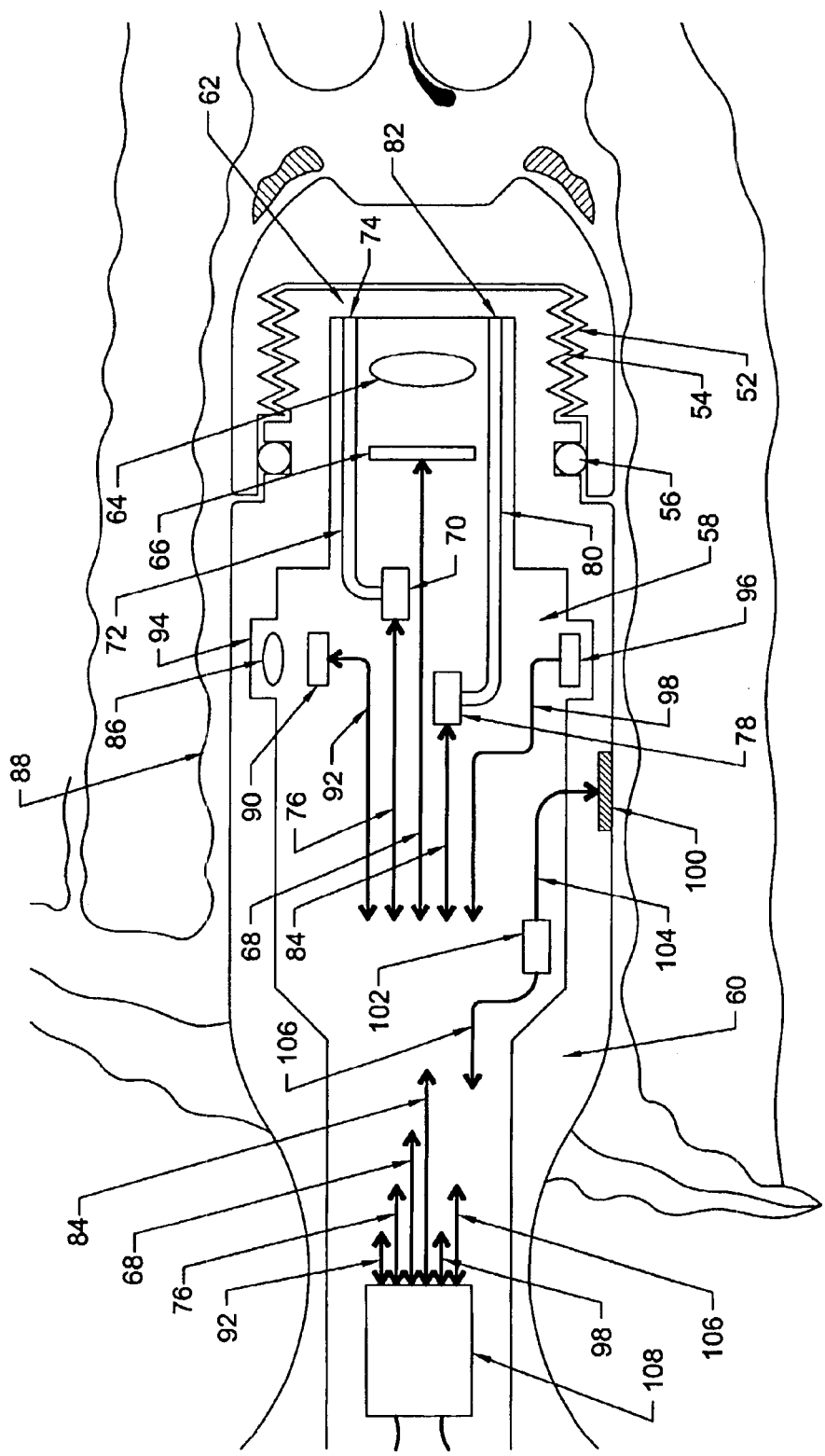
FIG. 2 shows an expanded section view of the Personal Pelvic Viewer shown in FIG. 1.

FIGS. 1 and 2

A preferred embodiment of the Personal Pelvic Viewers™ (PPV™) is generally shown as element 2 of FIG. 1. The PPV is located in place for viewing within a portion of the female reproductive system generally designated as element 4 in FIG. 1.

FIG. 1 shows a section view of a portion of the female reproductive system with the female in a slightly "elevated lithotomy position". In this position, the female is lying on her back, knees raised, with knees to the left-hand direction FIG. 1, and with the torso on an angle having the head suitably elevated above the pelvic region. In this position, the torso is on perhaps on a 30 degree angle with respect to horizontal, the head is elevated, and the head would be in the right-hand direction in relation to FIG. 1. Such an elevated lithotomy position is shown in FIG. 11-1 on page 152 of Gage, 1995. If the female is lying on a bed, then putting two or three pillows under her upper back and shoulders results in a "half sitting position" which is a good description of this "elevated lithotomy position". Such an elevated lithotomy position is also shown in the book entitled "The New Our Bodies, Ourselves" in the photograph on page 563; and in the book entitled "Our Bodies, Ourselves for the New Century" in the photographs on page 271 and on page 591. However, the position of the female is not shown in FIG. 1 for the purposes of clarity.

The upper wall of the vagina 6 and the lower wall of the vagina 8 are shown in FIG. 1, and those walls are generally horizontal as depicted in FIG. 1 that is appropriate for the "elevated" lithotomy position" described above. Each such upper and lower wall of the vagina has muscles, tissues, nerves, etc. that are not shown in FIG. 1 for the purposes of simplicity. FIG. 1 shows the uterus 10, that has an internal void described as is the uterine body cavity 12, the cervix 14, the external os 16 that is the external opening of the cervix into the rear of the vagina, and an example of cervical mucus 18 exiting from the external os into the rear of the vagina 20. FIG. 1 also shows the posterior fornix 22 and the anterior fornix 24.

In FIG. 1, the PPV is inserted into the interior of the vagina generally designated by numeral 26. Other portions of the female anatomy depicted in FIG. 1 include the urethra 28, the urethral opening 30, the labium majus (or labia majora) 32, the labium minus (or labia minora) 34, which labia join together in the region having the clitoris 36, the vaginal introitus 38, and the region generally described as the perineum 40.

There are a few details of interest related to the particular section view depicted in FIG. 1. The section view in FIG. 1 is taken so that the PPV is in placed in front of the labium majus and labium minus located on the right-hand side of the body of the female as would be defined by the female herself. The numeral 32 shows the portion of the labium majus located vertically above the PPV in FIG. 1, and the numeral 33 shows the portion of the labium majus located vertically below the PPV in FIG. 1. Similarly numeral 34 shows the portion of the labium minus located vertically above the PPV in FIG. 1, and the numeral 35 shows the portion of the labium minus located vertically below the PPV in FIG. 1. The portions of the labium majus and labium minus which are located on the left-hand side of the female body as would be defined by the female herself are not shown in FIG. 1 for the purposes of clarity and simplicity. Also not shown in FIG. 1 are the structures related to the ovaries and the fimbriae of the fallopian tubes which are generally attached to the uterus perpendicular to the plane of the sectional view of the uterus shown in FIG. 1. The inventors have been careful to use only terms that have been defined in Sloane, 1993 and in Edge and Miller, 1994.

Accordingly, and with reference to FIG. 1, and while the female is in the "elevated lithotomy position", the female grasps the "handle portion" 42 of the PPV with the fingers of her right hand, if she is right-handed. In general, and while in the "elevated lithotomy position", the length of the arm of an average female is sufficiently long so that she may easily grasp and manipulate the "handle portion" of the PPV. She then locates the vaginal introitus, and inserts the standard front cap 44 of the PPV into her vagina. She slides the PPV into the vagina until it reaches a convenient viewing distance "X" away from the cervix. The PPV is entirely under the control of the female, and because various sanitary devices, such as tampons, are similarly introduced into the vagina, it is evident that the female would normally be able to follow this procedure. The smaller OD of the "handle portion" 42 of the PPV is useful in that upon full insertion, the outer portion of the vagina may "clamp down" on this smaller OD portion of the handle to positively hold the PPV into place within the vagina.

The front cap 44 of the PPV has a transparent front flat plate 46 for good image transmission that is recessed by distance Y (not shown) from the front of the cap of the PPV because of the recession region 48. Upon insertion into the vagina, the front cap of the PPV typically collects up various vaginal secretions. Further, the female may choose to lubricate the outer portions of the front cap of the PPV with substances like K-Y Jelly before insertion into the vaginal introitus. Therefore, it is anticipated that the leading edge of the front cap will collect up vaginal secretions, any lubricating substances present, etc. that are collectively designated by numeral 50 in FIG. 1. A purpose for the recession region 48 is to provide a clear viewing area through the transparent flat plate that is not contaminated by vaginal secretions, lubrications, etc.

FIG. 2 shows a blow-up portion of FIG. 1 that includes the region containing the front cap 44 of the PPV. The front cap of the PPV has threads 52 that match the corresponding threads 54 of the viewing end of the PPV, and an appropriate "O-ring seal" 56 to keep the void region 58 clear of secretions, etc. The main body of the PPV 60 possesses a transparent flat plate viewing window 62 that is made integral with the main body of the PPV using typical fabrication techniques used in the industry. In several preferred embodiments, the main body of the PPV is fabricated from a plastic or rubber-like substance, and the transparent flat plate viewing window 62 is made of transparent plexiglass or the like.

FIG. 2 shows a first optical system 64 that focuses the image of the cervix onto a first electronic imaging system 66. As an example, in one preferred embodiment, the first optical system 64 may be one or more simple lenses, and the first electronic imaging system 66 may be a charged-coupled device (abbreviated as "CCD"). The first optical system provides a means of properly focusing the image of the cervix onto the first electronic imaging system. Any focusing means, including movable lenses on geared racks, may be used for this purpose. The focusing means may provide a fixed focal length, or that distance may be controlled by a computer, or other means which are described below, to obtain proper focus. Standard apparatus in the optical focusing arts and the optical imaging arts are used to construct the first optical system and the first electronic imaging system. The first electronic imaging system 66 provides outputs, and obtains any inputs controls, via wire bundle 68. In another preferred embodiment, a miniature video camera manufactured for certain close-focus purposes may be substituted for the first optical system 64 and the first electronic imaging system 66 in FIG. 1, which video camera is identified by numeral 67 that is not shown in FIG. 1 for simplicity, which would provide similar outputs and received similar inputs as described above in this paragraph. For the purposes herein, the term "video camera" or "video camera means" shall mean the suitable combination of an optical system and corresponding imaging system to properly provide video images of the cervix or of the interior of the vagina as desired.

FIG. 2 shows first light source 70 that, in this case, is connected to light pipe 72 that delivers light to point 74 for basic illumination of the cervix. In a preferred embodiment, the first light source is a white light source, and the light pipe delivers the light to point 74 for illumination of the cervix through various plates and voids as is evident from the previous description. The first light source 70 obtains control signals, and provides any measurements of light levels, etc. through wire bundle 76.

FIG. 2 shows second light source 78 that in this case is connected to light pipe 80 that delivers special lighting to point 82 for special lighting of the cervix. In a preferred embodiment, the second light source provides a duration of illumination by ultraviolet light for purposes that will be described below. The second light source 78 obtains control signals, and provides any measurements of light levels, etc. through wire bundle 84.

The first optical system 64 and the first imaging system 68 are used to measure the images when, alternatively the first or second light source is used to illuminate the cervix. In some preferred embodiments of the invention, only the first light source is provided, and in other embodiments of the invention, two or more such light sources are provided. The light pipe 72 may be designed so that it does not terminate perpendicularly to transparent flat plate viewing window 62 at point 74 to avoid multiple reflections back into the first optical system 64. Similar comments apply to light pipe 80 terminating at point 82 to avoid multiple reflections. Further, the various flat optically transparent flat surfaces themselves may all be chosen to be at small angles with respect to one another to avoid such multiple reflections, although this is simply another minor variation of the invention.

FIG. 2 shows second optical system 86 that focuses the image of a portion of the interior of the vagina designated as element 88 onto an electronic imaging system 90. As an example, the second optical system 86 may be one or more simple lenses, and the second electronic imaging system 90 may be a charged-coupled device or "CCD". As before, the second optical system provides suitable adjustable focusing means to image the interior of the vagina onto the electronic imaging system 90. The focusing means may have a fixed focal length or may be controlled from a computer system (described below) to provide proper focus. The electronic imaging system 90 provides outputs, and obtains any input controls, via wire bundle 92. The portion of the main body of the PPV at the location designated as 94 is transparent so that the portion of the interior of the vagina 88 is properly observed by the optical image system 86. Observations may be obtained with the first, and or second light sources as defined above. In some embodiments, yet other light sources are provided for the specific illumination of the wall of the vagina. However, if the main body of the PPV 60 is made from materials such as plexiglass or the like, then adequate lighting will be available at the portion of the vagina 88 to be observed from the first and or second light sources.

PPV internal sensor and instrumentation package 96 provides measurements of one or more of the following quantities: temperature, pressure, and sound. The internal PPV sensor may also provide measurements of the relative amount of blood flow in the wall of the vagina using doppler shifted acoustic measurements, and other blood flow measurement techniques known in the ultrasound art. That information is provided as an output, and control signals are inputted, on wire bundle 98. The PPV internal sensor and instrumentation package is not necessarily in direct contact with the fluids within the vagina.

PPV external sensor 100 provides measurements on the fluids within the vagina including the ph; the salinity; the types and quantities of hormones present; the quantity of any blood present; the types and quantities of any bacteria present; the types and quantities of any viruses present; the types and quantities of any fungi present; and perhaps the presence or absence of sperm. This external sensor 100 may also provide measurements of the electrical and electrochemical signals generated by the interior of the vagina. In certain preferred embodiments of this invention it is intended that the PPV provide an inventory of the chemical and biological substances within the vagina. This external sensor is based on the many biosensors available in the industry and as described for other biological uses in the USPTO. External sensor 100 provides measurements to the external sensor instrumentation package 102. Outputs from the external sensor 100, and any control signals sent to the external sensor by the external sensor instrumentation package 102, are provided over wire bundle 104. The output of the external sensor instrumentation package 102, and any control signals sent to it, are provide via wire bundle 106.

Master system control 108 receives data from, and provides control signals, power, etc. to wire bundles 68, 76, 84, 92, 98, and 106. Master system control 108 also provides any of the following elements necessary to provide the desired operational features of the PPV: (a) it provides means of providing power from an internal source or from another external source, in other words it provides a "power source means"; (b) it provides any power and control signals to any the elements defined above; (c) it possesses electronics including any required analogue to digital converter devices to properly process the temperature, pressure, and other data received; (d) it can receive commands from the exterior from the PPV; (e) it can send any information necessary to the exterior of the PPV; (f) it can have one or more means to process information, ie., it can have at least one "processor means"; (g) it can have one or more computers to process information, and/or interpret commands, and/or send data, ie., it can have one or more "computer means"; (h) it can have one or more means for data storage; (i) it can have one or more means for nonvolatile data storage if power is interrupted, ie., it can have one or more "nonvolatile data storage means"; (j) it can have one or more recording devices, ie., it can have one or more "recording means"; (k) it can have one or more read only memories, ie., it can have one or more "read only memory means"; (l) it may have one or more electronic controllers to process information, ie., it may have one or more "electronic controller means"; (m) it can have one or more actuator means to change at least one physical element of the device in response to measurements within the PPV, and/or commands received from the exterior of the PPV; (n) it can have one or more means to take samples from within the interior of the vagina and or cervix under the control the master control system using suitable instrumentation within the PPV or external to the PPV; and (o), it can have one or more means to introduce acoustic signals or vibrations into the vagina for a variety of purposes, including for the purposes of transvaginal imaging while the PPV is in place within the vagina.

Therefore, the master system control 108 provides all the electronics, computer, memory, and data communications functions necessary to enable the PPV to carry out the above functions and the below enumerated functions.

In accordance with the above, FIG. 2 has defined elements 52–108. Except for element 108, these are not enumerated on FIG. 1 for the purposes of clarity and simplicity. FIG. 1 is already crowded, and of these elements 52–108, only element 108 is shown again in FIG. 1.

Returning to FIG. 1, the master system control 108 is suitably labeled. It sends information out of the PPV via wire bundle 110 that is internal to the PPV and through wire bundle 112 that is external to the PPV. At a minimum, a waterproof seal 113 prevents contamination of the interior of the PPV with vaginal secretions, lubricants, etc. The wire bundle 112 is connected to the remote transceiver 116. Wire bundle 112 is perhaps 10 feet long, made of very flexible material surrounding multiple insulated electrical conductors, and is attached to mating electrical connectors 114 that in turn connect the wire bundle to the remote transceiver 116. The remote transceiver 116 may be conveniently placed adjacent to the torso of the female in the "elevated lithotomy position" who is performing the self-examination with the PPV. It is important that the PPV be washable and capable of being disinfected with agents such as alcohol or anti-bacterial soaps. The PPV may be placed into a dishwashing machine and suitably cleaned for re-use by the individual female. The mating connectors 113 may be disconnected, and the entire PPV along with wire bundle 112 may be washed by hand and submerged into alcohol for cleaning. The entire PPV with attached wire bundle 112 is water proof and may be sterilized. With suitable designs, it could be boiled in water for complete sterilization if desired.

In a preferred embodiment of the invention, the remote transceiver 116 obtains its power from several ordinary flashlight batteries, small 9 volt batteries, or the like. The remote transceiver 116 possesses remote infra-red ("IR") transceiver element 118 that sends the information and video images via encoded infra-red light to the monitoring system. That infra-red light sent to the monitoring system is designated as element 120 in FIG. 1.

The base station transceiver 122 has its base IR transceiver element 124 that receives the measured information and video images encoded by infra-red light. The base station transceiver then provides this measured information and video images to the visual display unit 126 via wire bundle 128. It should be noted that for the purposes herein, a "wire bundle" may be comprised of insulated copper wires, cables of the nature used for cable TV, or optical fibers, or a combination of any of the above.

In a preferred embodiment, the visual display unit 126 is an ordinary television set monitor. The visual image on the TV set monitor is generally designated as element 130 in FIG. 1 that in this case, is the visual image of the cervix as observed by the PPV inserted into the vagina as depicted in FIG. 1. The images of the cervix 14, the external os 16, and the cervical mucus 18 are clearly evident in the image displayed. The monitor also displays data, such as the temperature within the vagina that is, in this case "T=98.4° F.". This image may be recorded on the associated VCR with TV control that, in this preferred embodiment, is designated as element 132 as appropriate if the visual display unit 126 is an ordinary television set monitor. A video recording may be obtained of the visual inspection of the vagina with the PPV. The video recording may be done on ordinary VHS tape for example. In this case, the controls for the TV monitor are provided by the "VCR with TV Control" as one alternative for element 132. The measured information is also presented on the visual display. Any sounds measured within the vagina may be broadcast over speakers.

In another alternative preferred embodiment of the invention, the visual display unit 126 is instead a CRT monitor of a computer system, or the like. In this embodiment, the computer is used to provide information to the visual display unit 126. In this embodiment, element 132 is not the VCR as described above, but instead is a computer. The computer receives commands from the keyboard 134 via wire bundle 136. In yet other embodiments, the keyboard may be replaced with a speech command decoder responsive to spoken commands, that in this case, could be very convenient. As stated earlier, the computer may be used to provide proper focus of the interior of the vagina or of the cervix in several preferred embodiments of the invention.

In some cases, the images and information obtained by the female that are stored in the computer could, solely at her choice, be forwarded to a physician for additional advice via the internet through cable 138 connected to internet driver 140 that in turn provides data to the internet 142. Thus, solely at the choice of the female, she is able to obtain visual images of her cervix in the privacy of her own home, view them conveniently herself, and forward them to her physician. Again, any of these steps is totally up to her, and it is completely under her control. Any type of internet means may be used including internet means using telephone wires or wireless internet means.

In this embodiment of the invention, the CRT monitor and all related electronics obtains its power from the AC power grid generally designated by element 144 in FIG. 1. In this preferred embodiment, the computer 132 is connected to the visual display unit 126 via cable 146.

In this embodiment, the computer may determine that certain images or measurements need to be repeated because of some type of error in the data, for example. So, commands may be sent from the computer to the base station transceiver 122 and its base IR transceiver element 124 which transmits infra-red signals shown as element 148 to the remote transceiver element 118, so that signals are sent onto the master system control 108 that would, in turn, direct the PPV to perform repeated measurements.

In the above described embodiments, it is evident at this point that remote transceiver element 118 and the base IR transceiver element 124 use infra-red light for data communication. However, any bidirectional data communication scheme may be used including low power radio frequency (RF), low power microwave frequency, or any of the types of low power bidirectional data transmission schemes what are being used for wireless internet data communication and high speed data communication of any type. Any wireless data communications hardware and protocol may be used for this purpose. The lower power transmitters are best suited for this application because this absolutely minimizes the chances of any safety related problems. The entire electronics, communications, electronic imaging, and optical arts that are on file in the Library of Congress as it stands today is incorporated herein in its entirety by reference. In simple devices, one-way wireless data communication links can also be used. However, in other embodiments of the invention, all of these wireless links can be replaced with a fiber optic links, coaxial cable links, or with just ordinary copper wiring that use any number of communication protocols that have been described in the literature relating to the filed of data communications.

There is additional safety to be obtained if the remote transceiver 116 is battery operated and not otherwise connected by conducting copper wires or cables to the monitoring system. In such a situation, the remote transceiver 116 is "electrically isolated" from the AC power grid. Such electrical isolation precludes many types of electrical hazards associated with malfunctioning electronics otherwise connected to the AC power grid; precludes hazards associated with wiring mistakes in buildings; precludes hazards during lightening storms; and precludes dangerous types of "ground loops" due to a variety of design and environmental interference problems. Further, having the remote transceiver 116 located on the bed adjacent to a female performing self-examination with the PPV is certainly convenient, and allows the female to place that remote transceiver without having to "fight with" long cables, etc. In this preferred embodiment, the battery powers the transceiver and provides all the power required for the video camera and other devices located within the Personal Pelvic Viewer (PPV).

It is now necessary to describe a few additional details. In the following, it will be assumed that the preferred embodiment described shall apply to the computer attached to a CRT. The PPV has a hand-operated button 150 below a flexible covering 152 that is integral to the body of the PPV, a switch element 154, and wire link 156 to master system control 108. At the discretion of the female, this button may be used to begin recording the visual images and the data after the PPV has been properly positioned within her vagina. In one embodiment of the invention, "one click" starts the video recording, and the following "second click" stops the video recording. Various other schemes are possible. In another embodiment of the invention, perhaps it is desired to have one short click perform a "still frame" image of what was on the visual display. Perhaps it is desired to have two long clicks begin the storage of a long series of visual images. Accordingly, these are various versions of "hand operated control means for the PPV". If a speech command decoder is used instead of, or in addition to the keyboard 134, then this would provide "verbally operated control means for the PPV". For the record, element 134 includes the following possibilities: just the keyboard, just the speech command decoder, and both the keyboard and the speech command decoder.

Such a series of long visual images accompanied with sound and pressure readings vs. time might assist the female to understand her own orgasmic response and its relevance to any reproductive problems she might have. At the least, such images accompanied by sound and pressure would be educational.

With respect to FIG. 1, an end plug 158 is used to seal the PPV after final assembly. It has a key-way 160 for installation at the factory, threads 162 engaging threads 164 in the main body of the PPV, and suitable O-ring seal 166. However, in other embodiments, the PPV may be assembled to be one monolithic one-piece assembly by gluing together certain portions of the body of the PPV.

Proposed Cervical Cancer Detection with the PPV

It is the opinions of the inventors that many of the above embodiments of the invention might allow the female in certain circumstances to self-diagnose the initial appearance of cervical cancer using the following procedures. Below described are two such procedures.

First New Proposed Procedure to Detect Cervical Cancer

This proposed first new procedure is described in the following steps to detect cervical cancer:

1. Choose a PPV with a first light source that is a white light source for viewing the cervix that has a second ultraviolet light source for viewing fluorescent optical emissions from the cervix.
2. Insert the PPV into the vagina having first light source on and second light source off. View the cervix, and record the view of the cervix in a in a "first video recording".
3. Remove the PPV from the vagina.
4. Douche the vagina with a "particular liquid", where this particular liquid binds to cancerous cells and normal cells in a manner such that when illuminated with ultraviolet light, the cancerous cells and the normal cells can be determined by observation under ultraviolet light.
5. Insert the PPV into the vagina having first light source off and second light source on. View the cervix, and record the view of the cervix in a "second video recording".
6. Remove the PPV from the vagina.
7. Compare the "first video recording" with the "second video recording" to detect if any cancer cells are present, and if so, make an estimate of the region of the cervix affected by cancer.

It should be noted that similar procedures may be used on certain areas of the vaginal wall using the second optical system. Further, the "first video recording" and the "second video recording" may essentially be a "first still image" and a "second still image"—just like comparing two photographs. The point is that using one or more light sources, and a douche procedure between the initial insertion of the PPV and the final insertion of the PPV may be used by the female herself at her own home to screen for cancer. Such a procedure may be criticized as being prone to error. However, the so-called Pap smear is not accurate all the time.

With respect to the accuracy of Pap smears, please refer to Planned Parenthood Federation of America, Inc., 1996, page 311 that states: "Pap test screening is not perfect. Fifteen to 30 percent of those who are tested are found to have normal results when in fact there are abnormal cells present". This is the case involving "false negatives". False positives, involving Pap smears, results in more disastrous outcomes in the view of Dr. Robert S. Mendelsohn, an MD. In his book, that is the reference of Mendelsohn, 1981, I quote the following excerpt from page 41:

"My concern about these examinations, and the tests that are routinely associated with them, is not simply that they are largely worthless. I am concerned because too often they lead to physical damage and even death.

The Pap test is a classic example of this. Although it had never been subject to adequate study to determine its effectiveness, this test for cervical cancer was eagerly accepted by Modern Medicine. A 1973 study found that more than half of all American women over age seventeen had taken the test during the previous year.

Gynecologists welcomed the Pap test because it gave them access to their patients at least once a year. Although numerous studies questioned its value, doctors had no incentive to discourage annual testing, because it provide them with so many opportunities to intervene."

Mendelsohn, 1981, on page 43 further states:

"I realize that these are isolated examples from which no scientific conclusions can be drawn. I cite them merely to dramatize the reasons routine examination and testing of apparently healthy people is so hazardous to their health. It is because they lead to radical medical or surgical intervention based on tests that are suspect at best and grossly inaccurate at worst. They also lead to sloppy medical practice in which inadequate tests are substituted for careful clinical evaluation and sound medical judgement."

This view is reinforced in a recent article in Time Magazine, Dec. 13, 1999, page 74–76 entitled "Doctors'Deadly Mistakes" and "Medical errors kill up to 98,000 Americans yearly . . . ". It is based on the 1999 report from The Institute of Medicine, a branch of the National Academy of Sciences, entitled "To Err is Human, Building a Safer Health System". That report speaks for itself.

Second New Proposed Procedure to Detect Cervical Cancer

In the second procedure, steps are followed that resemble normal colposcopy procedures in gynecological determination of cervical cancer. Please refer to Rymer, et. al, 1997, pages 7–8. FIG. 10 therein shows a female being observed in a colposcopy clinic. FIG. 11 shows a "colpophotograph of a normal cervix". FIG. 12 shows a photograph "Exposing the squamocolumnar junction" following the application of "5% acetic acid to stain the abnormal areas white (acetowhite)." Therefore, photographic examination before and after shows evidence of cervical cancer. In the case of colposcopy, page 7 of this reference states: "The colposcopy (FIG. 10) is a binocular microscope. An illuminated, three-dimensional view of the cervix is obtained, magnified between 6 and 40 times (FIG. 11). This technique identifies both the severity of the abnormality giving rise to an abnormal smear and also the position on the cervix. Hence, it allowed the clinician to assess the suitability for local ablative therapy."

Accordingly, in this new proposed second procedure is described as follows:

A. Choose a PPV with a first light source that is a white light source for viewing the cervix.

B. Insert the PPV into the vagina having first light source on. View the cervix, and record the view of the cervix in a in a "first video recording".

C. Remove the PPV from the vagina.

D. Douche the vagina with a "particular liquid", where this particular liquid binds to cancerous cells and normal cells in a manner such that when illuminated with the first light, the cancerous cells and the normal cells can be determined by observation under the first light. In analogy with normal colposcopy, have the female douche with a 5% acetic acid solution.

E. Insert the PPV into the vagina having first light source on. View the cervix, and record the view of the cervix in a "second video recording".

F. Remove the PPV from the vagina.

G. Compare the "first video recording" with the "second video recording" to detect if any cancer cells are present, and if so, make an estimate of the region of the cervix affected by cancer.

Scott, et. al, 1999, also states on page 527 with respect to colposcopy the following three paragraphs which are quoted below:

"Colposcopy aids in examining the visible portion of the female reproductive tract (i.e., vulva, vagina, cervix). This technique complements cytologic evaluation and may be able to localize the source of abnormal cells seen on cytology.

Vulvar diseases amenable to colposcopic evaluation include HPV infections, herpes genitalis, and preinvasive cancers. The magnification afforded by the colposcope may aid in the selection of areas for biopsy.

The application of 3% acetic acid for 3 to 5 minutes may also help defined abnormal areas that typically turn white and display sharp borders (i.e. acetowhite epithelium). The colposcope may also aid in the recognition of clinically inapparent vaginal intraepithelial neoplasia or HPV infection. These lesions are also characterized by acetowhite epithelium.

Colposcopy is most commonly used for evaluating the cervix in patients with an abnormal Pap smear. After it is visualized and excess mucus is gently removed with a dry cotton ball, the cervix is treated with 3% to 5% acetic acid. As noted, flat condylomata or dysplastic areas turn white or develop a vascular pattern with a mosaic appearance or punctuation. The squamocolumnar junction and transformation zone are then thoroughly inspected, and a biopsy of suspicious areas is performed. In addition, nonpregnant patients with an abnormal Pap smear should have an endocervical biopsy. Bleeding occurring as a result of the biopsy can easily be controlled with ferric subsulfate (Monsel solution)."

From the above, it is evident that it is likely that the PPV may be used to determine the presence or absence of cervical cancer in some fraction of the cases. In any event, if the female could carefully observe her own cervix and vagina, perhaps she could observe early warning signs.

It is possible that simple direct observation of her cervix can directly detect precancerous conditions in at least some women. For example, on page 75 of Stoppard, 1994, it states the following:

"The second most common cancer affecting women, cervical cancer is one of few that has a long and well-defined precancerous stage, which doctors are able to detect during a PAP SMEAR."

There are two side-by-side photographs on page 75 of Stoppard, 1994, that are described as follows under the title of "The vulnerable cervix" that are quoted as follows;

"The picture on the left shows a healthy cervix, while that on the right show one with precancerous cells. Cervical cancer occurs mainly in the 25–35 age group, and there appears to be a link with the presence of genital warts in the vagina or on a partner's penis."

In the opinions of the inventors, it would be very difficult for a female not to be able to determine a change between two images shown on that page 75—provided she had knowledge of what her cervix looked like in time before and after a great change. Therefore, it may be possible for many females avoid the douching procedures in the above defined first and second new proposed procedures to detect cervical cancer and/or to detect precancerous conditions. These new procedures are defined as the new third and fourth procedures respectively to detect cervical cancer and/or to detect precancerous conditions in the cervix. However, these third and fourth procedures are not listed below for brevity.

In any event, and provided that a woman otherwise follows all normal suggestions by the medical profession, there is certainly little risk in becoming familiar with her own body and observing her uterus, vagina, and vulva for visible changes from what appears normal to her.

PPV Used to Assist Understanding Infertility Problems

If the female is having difficulty becoming pregnant, then perhaps as a first step she might wish to understand her own biology. Accordingly, she could insert the PPV once a day, take a "still frame" image of her cervix each time, take her vaginal temperature each day with the PPV. Then, each "still frame" and each temperature reading would be sent to the computer. The computer would then compile a "one minute video" that corresponds to one of her "periods". This "one minute video" corresponds to the female's "monthly" cycle that shows how the cervix behaves during the cycle along with a plot of the temperature within the vagina.

To see what such a "one minute video" might look like, please refer to Gage, 1995. There are 8 pages of photographs inserted between page 128 and 129 of Gage, 1995. In particular, there is a series of photographs beginning on the page entitled "Changes During the Menstrual Cycle". This series of photographs is described as follows: "This woman is 29 years old and has no children or abortions." The "one minute video" would show a series of images that look continuous to the human eye that would proceed through the entire menstrual cycle. On the next page is another series of photographs described in part: "This woman, age 46, had her first period when she was 14 years old." And there is one more series of photos on the next page described in part: "This woman is 19 years old."

This process could be repeated during a first cycle, a second cycle, and a third cycle. Such a series of images could diagnose heretofore difficult or impossible problems to detect. For example, what happens if the os does not open in proper synchronization for fertilization with ovulation, as evidenced from the basal temperature change? In current practices, such a failure would not be detectable. However, this information in the hands of the female could be used to enhance her chances of becoming pregnant. If there is a problem with synchronization, perhaps the husband would be requested to have sex during a very narrow window of time when pregnancy can occur.

The more information provided by the PPV, the better for diagnosing complex infertility problems. For example, cervical images, temperature, ph, and the presence or absence of certain fungi could be correlated with achieving pregnancy. There are many variations of methods to promote pregnancy using measurements provided by the PPV.

Similar comments apply to the female being able to prevent pregnancy using the typical "rhythm method".

For example, in the case of a woman practicing the "rhythm method", please refer to the series of photographs following page 129 in Gage, 1995 on the page entitled "Changes During the Menstrual Cycle". On one photograph it states: "DAY 14. She thinks she ovulated today. The os is open and there is clear, fertile mucus coming out. The cervix is very light pink in color". This is apparently an optimum situation for conception. Contrast this with the photograph labeled: "DAY 22. The os is closed and there is more whitish secretion on her cervix." It is evident that if a woman more clearly understood her cycle, then she could perhaps either enhance her probability of conception, or reduce the probability of conception—entirely at her own discretion.

As another point, please refer to the series of photographs in Gage, 1995 following page 129 having the legend reading: "This woman is 19 years old". This page further states:
"She has no children and has had one abortion. She is not having a menstrual cycle because she is taking birth control pills.* She has intervals of bleeding from drug withdraw that last approximately five days. There is no significant difference in the appearance of her cervix from one day to the next, due to the fact that the Pill is suppressing the normal menstrual cycle."

This page 129 in Gage, 1995, defines the "*" as follows:
"* The Pill Cycle: A woman takes a pill each day for 21 days. During this time most women do not have bleeding. Then she stops taking pills for seven days, or takes sugar pills instead. Within the next day or two (day 22 or so) most women get breakthrough bleeding which is really drug withdrawal bleeding that results from abruptly discontinuing the hormonlike drug contained in the Pill."

Therefore, a female having knowledge of the appearance of her own cervix could detect if the birth control pill were failing to preclude the possibility of pregnancy. Such a failure, for example, might be evident in the opening of her os and the production of the clear, fertile mucus fluids while taking the birth control pills.

The importance of the appearance of cervical mucus to the enhance reproduction or for birth control purposes is described at length in Edge and Miller, 1994 on pages 209–232 in Chapter 11 entitled "Fertility, Infertility, and Contraception". For example, on page 227 it states:
"The cervical mucus (Billings or ovulation) method involves an evaluation of cervical mucus from the vaginal introitus to predict ovulation. Before ovulation, the cervical mucus is thin, clear, and watery. During or just preceding ovulation, the mucus becomes thicker, more abundant, and "stretchy" and can be pulled like taffy 5 cm or more (spinnbarkeit). Sperm survives well in this mucosal environment. A woman should analyze her mucus several times a day and keep an accurate record of monthly changes before using the characteristics of cervical mucus to predict ovulation. The fertile time begins with the appearance of the slippery mucus and lasts for approximately 72 hours. The characteristics of the cervical mucus can be change by sperm, water-soluble lubricants, contraceptive foams or jellies, and vaginal infections such a yeast infection or candidiasis . . . "

Edge and Miller, 1994, on page 232 further go on to state under the "box" prominently labeled with "PATIENT TEACHING":
"4. Have the woman describe and report monthly changes in mucus, especially the appearance of slippery, fertile mucus."

Cover for Insertion of PPV

Various types of "applicators" are typically used with tampons. For a listing, please refer to Rinzler, 1997, in the table labeled with "Comparing the Products: Tampons" on pages 52–56. Various applicators are described including a cardboard applicator having a "rounded tip". The tampon is pushed through the slots of the "rounded tip" upon insertion in the vagina.

By analogy, a waxed cardboard tube having a "rounded tip" with "slots" could be designed to cover the PPV in shown in FIGS. 1 and 2. That is called an "insertion cover for the PPV". That cover with PPV is inserted into the vagina to the desired depth. The cover is then removed leaving the PPV in place. This process would tend to avoid contamination of the optical surfaces at the end of the PPV by vaginal secretions, lubricants, etc.

In another variation, the PPV may be inserted into a non-lubricated "condom-like-cover". This "condom-like-cover" is intentionally designed to have slotted weak points on the front end. Then, the outer layer of the "condom-like-cover" can be lubricated. The PPV covered by the lubricated "condom-like-cover" can then be inserted into the introitus and into the vagina. Upon reaching the final depth, the female can "pull back" on the "condom-like-cover", while holding the PPV in place, and the "condom-like-cover" may be removed from the vagina. Again, this process would tend to avoid contamination of the optical surfaces at the end of the PPV by vaginal secretions, lubricants, etc. It is important that the "condom-like-covers" be clearly marked and identified so that nobody would use them as ordinary condoms because they might fail at an inopportune time.

Accordingly, the invention provides for many different "PPV covers" that provide initial covering of the PPV upon insertion into the introitus and then into the vagina.

Figure 3:
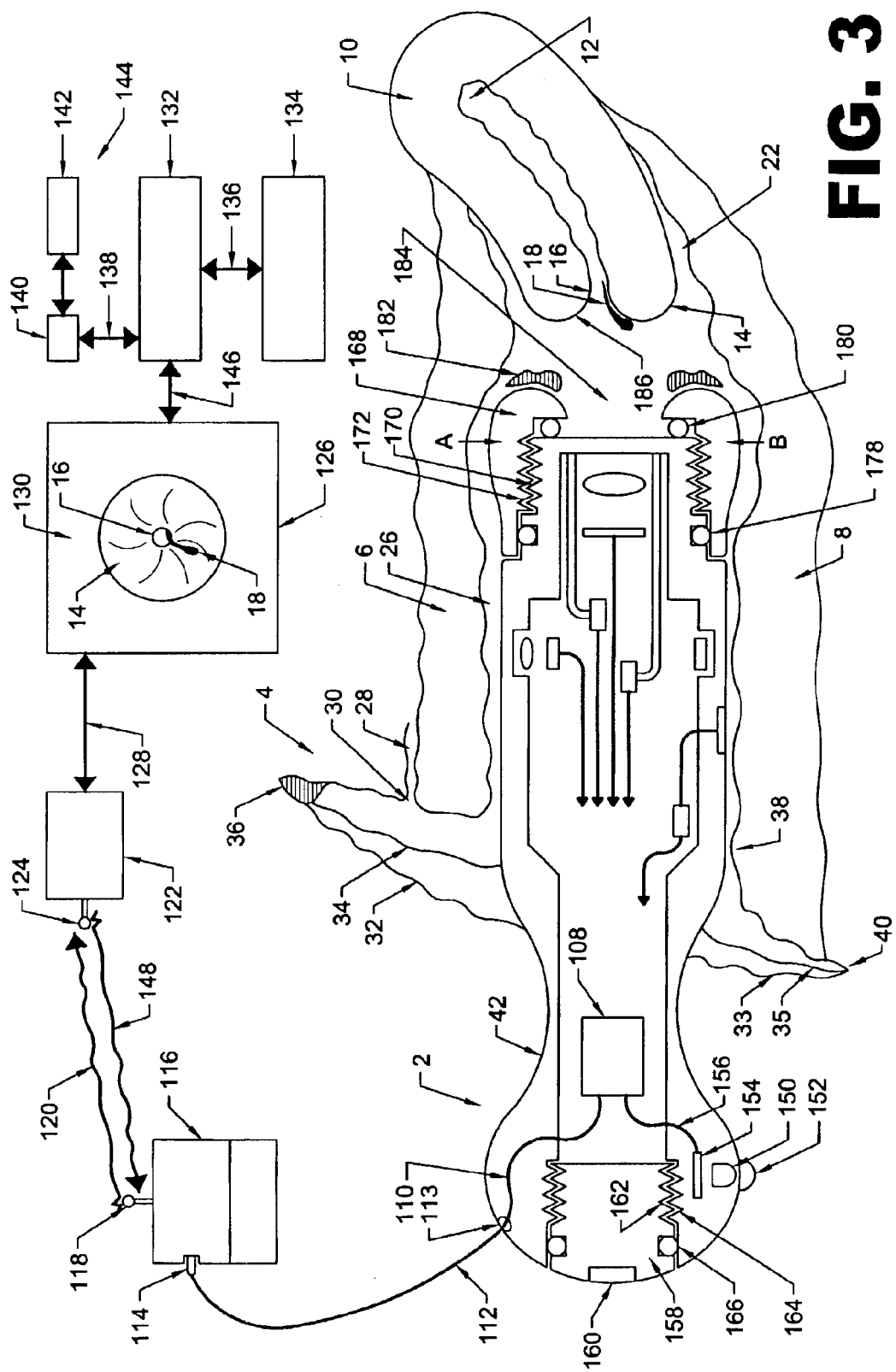
FIG. 3 shows a section view of another preferred embodiment of the invention which is similar to the PPV that is shown in FIG. 1, but in addition has an expanded front cap for improved viewing within the vagina.

Description of FIG. 3

FIG. 3 shows another preferred embodiment of the invention. Bivalve specula for pelvic examinations are constructed so that they expand after insertion into the vagina for a more clear view of the cervix and other organs. For a description of the art in this field as of 1999, please refer to Meehan, et. al., 1999. In particular, please see FIGS. 8A, 8B, 8C, and 8D in Meehan, et. al, 1999. The invention shown in FIGS. 1 and 2 could be modified so that structures resembling the "bills" of a bivalve speculum. However, a primary goal of the PPV is to provide a lone female the ability to observe her own vagina without the aid of another party, or without undue complexity. Such complexity might include mechanical or actuation means to open her vagina. An air operated "balloon type device" on the outside of the PPV could be used. Such devices are known in the field of gynecology. For example, see Meehan, 1999.

However, it is well known that the vagina, and the introitus of the vagina are extremely flexible and can expand to quite large sizes—provided that the female herself is in control. For example, inspect many "adult toys" used for enhancing the sexual pleasure of females, and many of such "adult toys" are circumferencially quite large. However, it is known that with sufficient care, patience, the lone female may comfortably insert quite large objects into her own vagina. Of course the process of birth and the recovery of the vagina after birth is a testimony to the flexibility of the vagina.

Accordingly, FIG. 3 shows a PPV with an enlarged front cap 168 that tends to expand the interior portion of the vagina in the region near the cervix an improved and unobstructed viewing by the PPV. All elements through element 166 elements in FIG. 3 have been previously described. Element 168 is an enlarged front cap that is chosen so that with sufficient care, preparation, and patience, an average female can insert this enlarged front cap into her introitus and then into the vagina.

The maximum lateral dimension of the enlarged front cap 168 is given by the dimensions of cross section AB in FIG. 3. This maximum lateral dimension will NOT be larger than the lateral dimensions of "adult toys" routinely commercially available. Further, the outer portion of the enlarged front cap may be made from very flexible rubber of the type typically used in many such adult toys. Such flexible rubber would make the insertion of the enlarged cap into the introitus more comfortable. Mating threads 170 in the PPV and 172 in the cap allow the oversize front cap to screw onto the PPV.

In FIG. 3, the enlarged front cap must be firmly screwed into place on the body of the PPV so that this enlarged front cap does not fall off within the vagina upon removal of the PPV from the vagina. (However, the front cap should have rounded edges on all portions of the cap should that occur and removal by hand be required.) Accordingly, a preferred embodiment provides for an inner portion of the enlarged front cap to be strong plastic that is bonded to soft rubber on the exterior of the enlarged cap for reasons already cited, although such as "laminated" structure is not shown in FIG. 3 for simplicity. For future reference, element 174 is reserved for the inner hard plastic portion of such an enlarged front cap having the threads in the cap 172 and element 176 is reserved for the outer soft rubber component of that enlarged cap, although elements 174 and 176 are not shown in FIG. 3 for simplicity.

In FIG. 3, rear O-ring 178 seals the enlarged front cap against the body of the PPV to the left-hand side in FIG. 3, and front O-ring 180 seals the enlarged front cap against the transparent flat plate viewing window 62 that is made integrally with the main body of the PPV. Typical O-ring fabrication processes are used. A reason for this construction allows the female to simply replace the standard front cap 44 with enlarged front cap 168—should she choose do so. The standard front cap 44 and the enlarged front cap 168 have suitable O-rings seals to keep vaginal secretions, etc. from the threads. However, the caps may be removed and cleaned if desired using techniques already described above.

Standard "K-Y® Brand Jelly", a personal lubricant manufactured by Ortho-McNeil Pharmaceutical, Inc., Raritan, N.J., may be used by the female to assist the insertion of the enlarged front cap into her introitus. Element 182 shows some K-Y jelly and other vaginal secretions on the forward portion of the enlarged cap. Recession region generally identified with element 184 in FIG. 3 is designed to minimize contamination into the viewing area by such K-Y jelly and by other vaginal sections. Such a construction will optimize the clarity of the uterus and the visual observation of any imperfections or suspicious areas on the uterus as identified with element 186 in FIG. 3.

It is also worthwhile to note that it might not help for insertion if the female is in a heightened state of sexual excitement. Please refer to Masters, Johnson, and Kolodny, 1995. In particular, please refer in general to Chapter 4 entitled "Sexual Physiology" in particular to FIG. 4.2 on page 76 entitled "Internal Changes in the Female Sexual Response". The terms defined in that Chapter 4 shall be used in this paragraph and elsewhere as appropriate. In the "plateau phase", the introitus becomes tighter because of increased blood flow, and this in part forms the "orgasmic platform". On page 78, of that Chapter 4 it states in part: "During the plateau phase in women prominent vasocongestion in the outer third of the vagina causes the tissues to swell. This reaction, called the orgasmic platform, narrows the opening of the vagina by 30 percent or more . . . " Therefore, if the orgasmic response of the female is to be observed, and if the PPV with an enlarged front cap is to be used, then perhaps it might be wise to first insert the PPV into the vagina, and then begin the process of achieving orgasm. It might also help if the female were to be in the "resolution phase" before it is removed. Before attempting to observe the female orgasm with the PPV, it is recommended that the female become acquainted with the processes involved as described in FIG. 4.2 and in many other books.

Simplified PPV

The inventors had conceived of the simplified form of the PPV some time ago. The inventors had disclosed this simplified PPV under confidentiality to several other parties. The simplified PPV has the following elements:

1. A PPV with at least one light source and one video camera within the vagina.
2. A PPV with at least a one directional wireless transmitter. For example this would include a one-way infra-red (IR) transmitter.
3. A suitable wireless receiver and a display in the form of a TV or a computer screen.
4. Preferably, the IR transmitter would be located in the handle of the PPV or in a box attached by a flexible cord as described above.

No separate figure is shown for this "simplified PPV", but the elements have been previously described in relation to FIGS. 1, 2, and 3. Instead of the IR transmitter in the above, a low power radio transmitter or a low power microwave transmitter can be used instead.

Simultaneous View of Perineum

Another embodiment of the invention uses the PPV in combination with yet another video camera whose function is to observe the portion of the perineum above the PPV.

In this embodiment, yet another very small video camera is located integral within "handle portion" of the PPV 42. This small video camera, is comprised of a third optical system 188 and a third electronic imaging system 190 (elements not shown in figures for simplicity). The purpose of this third video camera system is to provide images of the inner labium, outer labium, the urethral opening 30, and the clitoris that are located above the portion of the handle of the PPV inserted into the vagina. Such images may be provided on a split screen display.

As the PPV is rotated in the vagina, a 360 degree close-up view of the perineum may be obtained for the visual inspection of this region for that is a part of a normal gynecological examination. For example, please see Luckmann, 1997, under "Performing the Adult Physical Examination", and in particular under "f. Female Genitalia . . . " on pages 145–147.

Further, observation of the swelling of the labium majus, the color changes of the labium minus, and the changes in the physical shape and dimensions of the clitoris during the female sexual response is of interest for a variety of purposes, including for educational purposes.

Scientific issues may be resolved with this instrument. It is not now known if "female ejaculation" at orgasm pushes fluid through the urethral opening 30, or through the Skene's glans that are very close by, or if the a given female may ejaculate from one or more of these locations. For example, Sloane, 1993, on page 36 states: "But there are women who are concerned about expelling what seems to be a small gush of urine during intercourse, especially at orgasm. They are not urinating, but are probably experiencing a greater discharge from the paraurethral (Skene's) glands and the vulvovaginal (Bartholin's) glands—for them, a normal sexual response." Such a response may be different for different females. If a female wishes to understand more about her body, such observations correlated with vaginal pressure, sound, images of her uterus at orgasm would allow her to better understand her own sexual response. Such a response may be carefully observed while in the "elevated lithotomy position" with PPV in place and while also placing a hand-held "vibrator" against the clitoris for sexual stimulation.

Further, other embodiments of the invention provide for one or more "vibrator devices" to be incorporated within the PPV to further aid in such stimulation. If necessary, motion stabilization of the video images may be provided so that even though there are one or more acoustic stimulations, that the images are stabilized. And one more embodiment provides for computer based acoustic signals to be sent by the wireless communication system to the PPV to control the "vibrator devices" within the PPV to aid during sexual stimulation. Such acoustic signals include the provision of "base signals" from ordinary audio tapes or other acoustic signals related to music converted to acoustic signals sent to the PPV by a wireless commutation link. Such observations by a female would certainly be educational, if for no other reasons.

Women's Health and the PPV

The medical community has during the last decade generally recognized that a healthy sex life for women and men is important to their overall physical and mental health. Typical of such modern views is the following excerpt from the Chapter entitled "Women and Sexuality", on page 106 of Youngkin and Davis, 1998:

'Sexuality is inextricably woven into the fabric of a women's life and is an important aspect of her health. It is an integrated, unique expression of self that encompasses physiological and psychosocial processes inherent in sexual development, sexual response, sexual desire, view of self as a female including sexual orientation, and presentation of self to society as a woman.[1] Sexuality underlies much of who and what a person is, and it is an inherent, ever changing aspect of life from birth to death. It is expressed in different ways at different times—alone, with one partner, or with different partners.[2]

Although experts do not agree on a definition of sexual health or what constitutes normal sexual behavior, the World Health Organization definition provides a starting point: "Sexual health is the integration of somatic, emotional, intellectual, and social aspects of sexual beings in ways that are positively enriching and that enhance personality, communication and love".[3] Essential elements of this definition include a woman's capacity to live in a manner that is congruent with her personal and social ethic while enjoying and controlling sexual and reproductive behavior; the freedom from psychological factors such as guilt, anxiety, fear, shame and misconceptions that impair sexual response and hurt sexual relationships; and the absence of disease, illness, organic disorders or deficiencies that interfere with sexual function.[2] Integral to sexual health is an acceptance of one's self-concept, body image, sexual identity, and sexual orientation.

Sexual health is that emotional and physical state that allows enjoyment and the ability to respond to sexual feelings. In short, sexual health may be considered the physical and emotional state of well-being that enables us to enjoy and act on our sexual feelings.[4] Promoting sexual health is a legitimate role for health professional and an essential nursing function. The nurse practitioner or other primary care provided can have primary role in promoting and maintaining the sexual health of women.'

On page 114 under the subtopic of "Inhibited Female Orgasm" of Youngkin and Davis, 1998, it states:

"Women whose orgasmic difficulties have a physical basis should be treated for the underlying cause. Once physical causes have been corrected, the most common treatments of this problem are behavioral. For example, the women is taught to experience orgasm through a series of exercises that increase here awareness of genital sensations and masturbatory techniques.[52] Once she has experienced an orgasm through self-stimulation, she is taught to transfer this knowledge to a partner experience. Women with a partner may be given specific couples exercises to practice. Women with an orgasmic dysfunction may also benefit from information about female anatomy and physiology and the differences between male and female response cycles."

With regards to the sexual health of women, please also refer to the section in Sloane, 1993, entitled "Sexual Problems in Women" on pages 197–199 which states in part with respect to problems achieving orgasm: "One of the best ways to teach oneself to have an orgasm is by masturbating, but even knowing how to masturbate may not come naturally to women who have been taught since childhood that touching oneself is wrong and shameful. The very intense local stimulation that is derived by an electric vibrator may help to achieve orgasm initially." Sloane, 1993, in general emphasizes that "knowledge concerning the anatomy and physiology of the female orgasm" is important.

The above quotes in this paragraph are representative of much of what now is common practice in the medical community. A central them is that the overall health of the female and the sexual health of a female is enhanced by knowledge of her own reproductive organs and their response under sexual stimulation.

Accordingly, the female alone in her own home may view and investigate her own sexual cycle with the PPV inserted into her vagina. This sexual cycle is clearly explained in FIG. 4.2 on page 76 of Masters, Johnson and Kolodny, 1995, and the terms used in that FIG. 4.2 and in the related text on pages 70–86 will be used here and quotes will be used from this reference. Therefore, the female may view the following with the PPV having a first, second, and third optical system described above.

1. Excitement Phase: During the excitement phase, vaginal lubrication appears through the process of transudation. "Other changes also occur in women during the excitement phase. The inner two-thirds of the vagina expand, the cervix and uterus are pulled upward, and the outer lips of the vagina flatten and move apart . . . " "In addition, the inner lips of the vagina enlarge in diameter, and the clitoris increases in size as a result of vasocongestion."

2. Plateau Phase: During the plateau phase, the uterus elevates, and the vagina expands dramatically, a phenomenon called "tenting" that provides a region for the seminal pool. "During the plateau phase in women prominent vasocongestion in the outer third of the vaginal causes the tissues to swell. This reaction, called the orgasmic platform, narrows the opening of the vagina by 30 percent or more . . . " "The clitoris pulls back against the public bone". "The inner lips enlarge dramatically as a result of engorgement with blood, doubling or event tripling in thickness." "Once this reaction has occurred, vivid color changes develop in the inner lips." 'Masters and Johnson (1966) noted that if effective sexual stimulation continues once this "sex skin" color change appears, orgasm invariably follows. In more than 7500 cycles of female sexual response, an orgasm never occurred without the preceding color change of the inner lips.'

3. Orgasm Phase: "Orgasm in the female is marked by simultaneous rhythmic muscular contractions of the uterus, the outer third of the vagina (the orgasmic platform) . . . ". "The first few contractions are intense and closed together (at 0.8-second intervals). As orgasm continues, the contractions diminish in force and duration and occur at less regular intervals. A mild orgasm may have only 3 to 5 contractions, while an intense orgasm may have 10 to 15."

4. Resolution Phase: During the resolution phase, the uterus moves towards its original position, the orgasmic platform within the vagina gradually disappears, and the vagina returns to normal.

In the above, the "outer lips" are the labium majus (or labia majora), and the "inner lips" are the labium minus (or labia minora).

The first optical system of the PPV will provide views of the motion of the cervix and the os during the sexual cycle. Such images using different technology were provided in a television show on The Learning Channel in the series entitled "Intimate Universe, The Human Body" and in the particular episode of that series entitled "Building a Baby", that was copyright 1998, (hereinafter "TLC, 1998"), and presented by Dr. Robert Winston. It showed the remarkable images from inside the vagina of a woman. Those images clearly show that during the orgasm of the particular woman being filmed, the tip of her uterus dips repeatedly and rhythmically into the region of the vagina having the seminal pool—evidently because this increases the chances of insemination from an evolutionary point of view. In one segment of TLC, 1998, it appeared that a standard video camera was placed inside a glass or plastic "test tube" type device having a rounded end that showed distorted images within the vagina at orgasm. In another segment of this television show, it appeared that a standard video camera with a long focal length lens (perhaps 135 mm) was viewing the cervix at orgasm through a bivalve speculum located in place within the vagina.

The particular images described above had been previously obtained using different procedures than described herein. These images were obtained using different technology than that provided by the PPV in the original pioneering studies by Masters and Johnson, 1966. Regarding this academic study by Masters and Johnson, Sloane, 1993, states the following on page 189: 'They made observations during manual masturbation, during masturbation with a vibrator, during intercourse in several positions, while the breasts alone were stimulated without genital contact, and also during "artificial coitus" with a plastic penis containing a movie camera to record internal changes.' Regarding health matters, Sloane, 1993, further states on page 189 regarding the work of Masters and Johnson: "Use of the artificial penis also made possible observations that had clinical value in infertility problems and contraceptive research."

It is the opinions of the inventors that a PPV would provide such images much more clearly and under circumstances that are much more private and discrete for the female investigating her own body. The PPV will provide the female her own images that until now would have required a filming crew, a gynecologist, and facilities in a major scientific laboratory. The lack of privacy is the female is obvious in such a laboratory environment.

In addition to the above images during orgasm, the second optical system of the PPV may be used to monitor transudation and related phenomena.

The third optical system of the PPV may be used to observe the sexual cycle of regions of the perineum.

The PPV may also be used in the scientific study of the sexual response of the human female in the privacy of her own home—should she choose to participate in such a study. Any or all of the above signals could be provided through the internet to a laboratory for scientific study while the female is in the safety and security of her own home who chose to be part of such a study. With suitable attention to anonymity in the study, perhaps many females might wish to participate in such a scientific study. Perhaps if the beauty, and the stunningly complex physiological responses were better understood by the community at large, perhaps women in general might be accorded the same respect for their wondrous genitals as are accorded to the males for their more obvious genitals.

Perhaps the PPV could significantly benefit society in a number of ways. For example, if males better understood that the sexual response of the human female involves physiological responses and physical changes within her body that are equal to or greater than that of the male's, then women might be accorded additional respect and dignity for the wondrous anatomy of an adult woman. With respect to this particular subject, Masters, Johnson and Kolodny, 1994, under the subtitle of "Common Myths About Sexual Response" on page 86 state the following:

"One commonly held belief is that males have a greater sexual capacity than females. The reverse is actually true."

With the images from the PPV in her hands, any women could prove the validity of this statement to herself, or to anybody else she might choose.

Samples with the PPV

It is evident from the above that suitable modifications of the PPV may be made so that the female in the privacy of her own home might be able to take PAP smears from her cervix while viewing the sampling procedure with the PPV. There are many modifications to the above PPV's that would allow this. One simple modification is to provide an open hole along the length of the PPV through which the female could insert a spatula type device to sample here own cervix. Perhaps she could then treat these samples with a fixer, and send them to a laboratory for standard analysis. A photograph of such procedures, and an accompanying brief description, appear in Rymer, et. al., 1997, under the topic of "2. Investigative techniques" on pages 5–6.

Other Types of Displays

FIGS. 1, 2 and 3 contemplate the display of the visual image from the PPV on element 126. Again, element 130 is in some embodiments a TV monitor, and in others, is a CRT monitor of a computer system, or the like. Any type suitable display may be used for this purpose.

The views from the PPV may be presented on a "split-screen" display. For example, for example a TV monitor, or CRT monitor as they case may be, may have four equal size areas for display. Three of the areas may show images from the first, second, and third optical systems simultaneously. Data, such as temperature and pressure in real time as measured within the vagina may be displayed in the remaining fourth area. Simultaneous with all of the visual displays are sounds as measured within the vagina in real time.

However, yet other preferred embodiments of the invention contemplate using so-called "retinal displays" and the like. For the purposes herein, such displays are head-mounted devices that provide displays to the human observer. A "retinal display" may be used in combination with the other displays enumerated above or as the only display for several preferred embodiments of the invention. The "retinal display" may be used by the female during self-examination in the privacy of her own home. The "retinal display" may also be used by a gynecologist while using the PPV to perform internal visualization of the cervix, vagina, etc. and to perform other tests with the PPV.

Another embodiment of this invention provides for any device located within the human body for monitoring purposes that has any of the above wireless display and recording characteristics shown in FIGS. 1, 2 and 3. For example, most presently used internal visualization device for viewing within human body cavities are connected to other instruments by wires, cords, mechanical devices, light pipes, etc.

Accordingly, the invention herein provides the method of observation of interior body parts including at least the following steps: placing observation means within the body interior that obtains visual information; sending that visual information by at least one wireless communications means to a receiver attached a display system; and viewing the visual information on the display system remote from the interior of the body. Similar comments apply to methods of recording information. This method may also include at least one or more additional measurements described above.

In analogy, the invention herein also includes apparatus having the following elements: means located within the body interior to obtain visual information; wireless transmitter means within the body; wireless receiver mans outside the body; and display means to display the visual information obtained within the body. This invention not only pertains to the PPV, but to any instrument for measuring and recording information within the human body used in the medical sciences.

Yet another variation of the invention provides for views within the anal cavity. A slightly smaller OD version of the PPV may be inserted into the rectum and visual images obtained of the type described above. Such images are particularly relevant in studying the orgasmic response of the human female at orgasm. The device engineered for anal insertion is called the "Personal Anal Viewer™" that is abbreviated "PAV™". The distal end of the PAV would normally be inserted past the sphincter muscle into the interior of the anus for viewing. A suitable "stop" would be formed into the handle portion of the PAV so that the handle could not be inserted completely into the anus that would pose a potential retrieval problem. Many adult "toys" have such "stops" that prevent complete insertion into the anus.

Yet another variation of the invention provides for the simultaneous viewing of the interior of the vagina with the PPV and the interior of the anus with the PAV. Here, both the PPV and the PAV are independently connected to the remote transceiver 116 by separate wires. However, visual display on element 130 in FIG. 1 would then be a "split display", where the first image corresponds to the interior of the vagina and the second image corresponds to the interior of the anus.

Yet another variation of the invention provides for the simultaneous viewing of the interior of the vagina with the PPV, the simultaneous viewing of the perineum (see the above section entitled "Simultaneous View of Perineum"), and the simultaneous viewing of the interior of the anus with the PAV. In this case, the visual display would show three images. Such a system would be particularly useful to investigate the orgasmic response of the human female.

Yet another variation of the invention provides for the simultaneous viewing of the interior of the vagina with the PPV, the simultaneous viewing the perineum with the PPV (see the above section entitled "Simultaneous View of the Perineum"), the simultaneous viewing of the interior of the anus with the PAV, the simultaneous frontal view of the general genital area with a first standard video camera, the simultaneous close-up view of the nipples with a second standard video camera, and the simultaneous viewing with a third standard video camera of the entire body of the female. Such visual information would be very useful for studying the orgasmic response of the human female, a topic of considerable scientific interest at this time.

In view of the above description, a method of observation of the interior of the vagina by a lone female within a room including has been described that includes at least the following steps:

(a) the female places a sealed video camera means within her own vagina, whereby that means possesses a sealed transparent aperture so that the means may properly view the interior of the vagina and the cervix;

(b) obtaining video information from the video camera means;

(c) transmitting the video information by a wireless communications means to a receiver means attached to a monitor means located within the room; and (d) viewing the video information on the monitor means to view the interior of her own vagina.

Here, the monitor means may be a television set or a computer monitor. The video information may be recorded by a recording means. The recorded video information may be forwarded by a data transmission means to a physician's office remote from the room, and the data transmission means may be the internet. Here, the video camera means obtains its electrical power from a battery power supply means. The wireless communication means may use infra red radiation, radio waves, or microwaves.

In accordance with the above, a Personal Pelvic Viewer has been described for viewing the vagina and cervix by a lone female in a room comprising:

(a) a sealed video camera means having suitable geometric dimensions to be placed within the vagina by the female, whereby the means provides video data, and whereby the means possesses a sealed transparent aperture so that the video camera means may view the interior of the vagina and the cervix of the female;

(b) a remote transceiver means that obtains the video data through an electrical cable attached to the sealed video camera means that transmits by a wireless data transmission means the video data to a base station transceiver means located within the room; and (c) electronic means to display video data obtained from the base station transceiver means on a monitor means for viewing by the lone female.

Here, the monitor means may be a television set or a computer monitor. The video data may be recorded by a recording means. The recorded video data may be forwarded by a data transmission means to a physician's office remote from the room. In one embodiment, the data transmission means is the internet. In one embodiment, the video camera means obtains its electrical power from a battery power supply means. The wireless communications means may use infra red radiation, radio waves, or microwaves.

In view of the above, a Personal Pelvic Viewer for viewing the vagina and cervix by a lone female in a room comprising:

(a) a sealed video camera means having suitable geometric dimensions to be placed within the vagina by the female, whereby the means provides video data, and whereby the means possesses a sealed transparent aperture so that the video camera means may view the interior of the vagina and the cervix of the female;

(b) means to provide the video data to a monitor system;

(c) means to display the video data to provide an image of the interior of the vagina and cervix to be viewed by the lone female within the room.

Here, the monitor system may be a television set or a computer monitor. The video data may be recorded by a recording means. The recorded video data may be forwarded by a data transmission means to a physician's office remote from the room. In one embodiment, the data transmission means is the internet. In one embodiment, the video camera means obtains its electrical power from a battery power supply means.

It is also evident from the above that the invention provides methods and apparatus for a lone female at home to inspect her own vagina and cervix to determine the presence of any foreign objects, including misplaced tampons, or condoms that may have slipped off during intercourse. It is further evident that the Personal Pelvic Viewer (PPV) may be used to determine the proper positioning of a cervical cap used for contraceptive purposes.

It should also be noted that recent advances make small camera systems of the type required for the PPV and the PAV feasible. For example please refer to the article entitled "A Fantastic Voyage Through Your Intestines" under "Developments to Watch" in Business Week dated Jun. 12, 2000, an entire copy of which is incorporated herein by reference.

The hand-held device that is inserted within the vagina is called the Personal Pelvic Viewer™ (PPV™) and is to become widely available through the internet sales and in stores currently selling "adult toys" commonly used for sexual purposes. Other sales outlets are also contemplated.

References

The following references were cited above. However, entire copies of the following references are incorporated herein by reference.

Edge, V. and Miller, M., the book entitled "Women's Health Care", Mosby, St. Louis, Mo., 1994

Gage, S., the book entitled "A New View of a Woman's Body", the Feminist Health Press, Los Angeles, Calif., 1995

Lauersen, N., and Whitney, S., "with" Stukane, E., the book entitled "It's Your Body", Perigee Books, The Putnam Publishing Group, New York, N.Y., 1993

Luckmann, J., Editor, the book entitled "Saunders Manual of Nursing Care", W. B. Saunders Company, Philadelphia, Pa., 1997

Masters, W. H., and Johnson, V. E., in the book entitled "Human Sexual Response", First Edition, Little & Brown, Boston, Mass., 1966

Masters, W. H., Johnson, V. E., and Kolodny, R. C., the book entitled "Human Sexuality", Fifth Edition, Harper Collins College Publishers, New York, N.Y., 1995

Meehan, et. al., U.S. Pat. No. 5,865,729 entitled "Apparatus for Facilitating Gynecological Examinations and Procedures" that issued on Feb. 2, 1999

Mendelsohn, R. S., the book entitled "Male Practice, How Doctors Manipulate Women", Contemporary Books, Inc., Chicago, Ill., 1981

Institute of Medicine, National Academy of Sciences, the book entitled "To Err is Human, Building a Safer Health System", "Advanced Copy", National Academy Press, Washington, D.C., 1999

Planned Parenthood Federation of America, Inc., the book entitled "The Planned Parenthood® Women's Health Encyclopedia", Crown Trade Paperbacks, New York, N.Y., 1996

Rinzler, C. A., in the book entitled "The Women's Health Products Handbook", Hunter House, Inc., Alameda, Calif., 1997

Rosenfeld, J. A., the book entitled "Women's Health in Primary Care", Williams and Wilkens, Baltimore, Md., 1997

Rymer, J., Fish, A. N. J., and Chapman, M., the book entitled "Gynecology" and "Color Guide", Second Edition, Churchill Livingstone, Edinburgh, U.K., 1997

Scott, J. R., DiSaia, P. J., Hammond, C. B., and Spellacy, W. N., Editors, the book entitled "Danforth's Obstetrics and Gynecology", Eighth Edition, Lippincott Williams & Wilkins, Philadelphia, Pa., 1999

Sloane, E., the book entitled "Biology of Women", Third Edition, Delmar Publishers Inc., New York, N.Y., 1993

Stoppard, M., the book entitled "Woman's Body", Carroll & Brown Limited, London, U.K., 1994

The Boston Women's Health Book Collective, the book entitled "The New Our Bodies, Ourselves", Simon & Schuster, New York, N.Y., 1992

The Boston Women's Health Book Collective, the book entitled "Our Bodies, Ourselves for the New Century", Simon & Schuster, New York, N.Y., 1998

The Learning Channel ("TLC"), the series entitled "Intimate Universe, The Human Body", in the particular episode entitled "Building a Baby", "a BBC/The Learning Channel Co-Production", presented by Dr. Robert Winston, 1998

Youngkin, E. Q. and Davis, M. S., the book entitled "Women's Health, A Primary Care Clinical Guide", Appleton & Lange, A Simon & Schuster Company, Stamford, Conn., 1998

What is claimed is:

1. A method of observation of the interior of the vagina by a lone female within a room including at least the following steps:
   (a) said female places a sealed video camera means within her own vagina, whereby said means possesses a sealed transparent aperture so that said means may properly view the interior of the vagina and the cervix;
   (b) obtaining video information from said video camera means;
   (c) transmitting said video information by a wireless communications means to a receiver means attached to a monitor means located within said room; and
   (d) viewing said video information on said monitor means to view the interior of her own vagina.

2. The method in claim 1 whereby said monitor means is a television set.

3. The method in claim 1 whereby said monitor means is a computer monitor.

4. The method in claim 1 where said video information is recorded by a recording means.

5. The method in claim 4 whereby said recorded video information is forwarded by a data transmission means to a physician's office remote from said room.

6. The method in claim 5 wherein said data transmission means is the internet.

7. The method in claim 1 wherein said video camera means obtains its electrical power from a battery power supply means.

8. The method in claim 1 wherein said wireless communications means uses infra red radiation.

9. The method in claim 1 wherein said wireless communications means uses radio waves.

10. The method in claim 1 wherein said wireless communications means uses microwaves.

11. A personal pelvic viewer for viewing the vagina and cervix by a lone female in a room comprising:
    (a) a sealed video camera means having suitable geometric dimensions to be placed within the vagina by said female, whereby said means provides video data, and whereby said means possesses a sealed transparent aperture so that said video camera means may view the interior of the vagina and the cervix of said female;
    (b) a remote transceiver means that obtains said video data through an electrical cable attached to said sealed video camera means that transmits by a wireless data transmission means said video data to a base station transceiver means located within said room; and
    (c) electronic means to display video data obtained from said base station transceiver means on a monitor means for viewing by said lone female.

12. The apparatus in claim 11 whereby said monitor means is a television set.

13. The apparatus in claim 11 whereby said monitor means is a computer monitor.

14. The apparatus in claim 11 where said video data is recorded by a recording means.

15. The apparatus in claim 14 whereby said recorded video data is forwarded by a data transmission means to a physician's office remote from said room.

16. The apparatus in claim 15 wherein said data transmission means is the internet.

17. The apparatus in claim 11 wherein said video camera means obtains its electrical power from a battery power supply means.

18. The apparatus in claim 11 wherein said wireless data transmission means uses infra red radiation.

19. The apparatus in claim 11 wherein said wireless data transmission means uses radio waves.

20. The apparatus in claim 11 wherein said wireless data transmission means uses microwaves.

21. A personal pelvic viewer for viewing the vagina and cervix by a lone female in a room comprising:
    (a) a sealed video camera means having suitable geometric dimensions to be placed within the vagina by said female, whereby said means provides video data, and whereby said means possesses a sealed transparent aperture so that the video camera means may view the interior of the vagina and the cervix of said female;
    (b) means to provide said video data to a monitor system; and
    (c) means to display said video data to provide an image of the interior of the vagina and cervix to be viewed by said lone female within said room.

22. The apparatus in claim 21 whereby said monitor system is a television set.

23. The apparatus in claim 21 whereby said monitor system is a computer monitor.

24. The apparatus in claim 21 where said video data is recorded by a recording means.

25. The apparatus in claim 24 whereby said recorded video data is forwarded by a data transmission means to a physician's office remote from said room.

26. The apparatus in claim 25 wherein said data transmission means is the internet.

27. The apparatus in claim 21 wherein said video camera means obtains its electrical power from a battery power supply means.

28. A personal pelvic viewer for viewing the vagina and cervix by a lone female in a room comprising:
    (a) a sealed video camera means having suitable geometric dimensions to be placed within the vagina by said female, whereby said means possesses a handle portion for use by said lone female to suitably grasp said means by hand for insertion within her vagina, whereby said means provides video data, and whereby said means possesses a sealed transparent aperture so that said video camera means may view the interior of the vagina and the cervix of said female;

(b) a remote transceiver means that obtains said video data through an electrical cable attached to said handle portion of said sealed video camera means that transmits by an infra red transmission means said video data to a base station transceiver means located within said room, whereby said remote transceiver means is located external to the body of said lone female; and (c) electronic means to display video data obtained from said base station transceiver means on a monitor means for viewing by said lone female.

29. A personal pelvic viewer for viewing the vagina and cervix by a lone female in a room comprising:

(a) a sealed video camera means having suitable geometric dimensions to be placed within the vagina by said female, whereby said means possesses a handle portion for use by said lone female to suitably grasp said means by hand for insertion within her vagina, whereby said means provides video data, and whereby said means possesses a sealed transparent aperture so that said video camera means may view the interior of the vagina and the cervix of said female;

(b) a remote transceiver means that obtains said video data through an electrical cable attached to said handle portion of said sealed video camera means that transmits by an infra red transmission means said video data to a base station transceiver means located within said room, whereby said remote transceiver means is located external to the body of said lone female, whereby said remote transceiver means receives its electrical power a batter power supply means located within said remote transceiver means so that it is electrically isolated from the AC power grid to avoid electrical hazards, and whereby said battery power supply means within said remote transceiver means also provides electrical power to said sealed video camera means through a cable attached to said handle portion of said sealed video camera means so that said video camera means is also electrically isolated from said AC power grid to avoid electrical hazards; and (c) electronic means to display video data obtained from said base station transceiver means on a monitor means for viewing by said lone female.

* * * * *